United States Patent [19]

Puttner et al.

[11] 4,297,361
[45] Oct. 27, 1981

[54] THIAZOLYLIDENE-OXO-PROPIONITRILES, INSECTICIDAL COMPOSITION CONTAINING THESE COMPOUNDS

[75] Inventors: Reinhold Puttner; Ulrich Bühmann; Harmut Joppien, all of Berlin, Fed. Rep. of Germany

[73] Assignee: Schering Aktiengesellschaft, Berlin and Bergkamen, Fed. Rep. of Germany

[21] Appl. No.: 151,109

[22] Filed: May 19, 1980

[30] Foreign Application Priority Data

May 17, 1979 [DE] Fed. Rep. of Germany ....... 2920183

[51] Int. Cl.³ .................. C07D 417/04; C07D 277/38; A01N 43/40; A01N 43/78
[52] U.S. Cl. .................................... 424/263; 424/270; 546/280; 548/146; 548/204
[58] Field of Search ................ 548/204, 146; 546/280; 424/263, 270

[56] References Cited

U.S. PATENT DOCUMENTS 3,661,920 5/1972 Hepworth et al. ................. 548/204
3,769,040 10/1973 Pittet et al. .......................... 548/204

Primary Examiner—Alan L. Rotman
Attorney, Agent, or Firm—Michael J. Striker

[57] ABSTRACT

A thiazolylidene-oxo-propionitriles of the formula

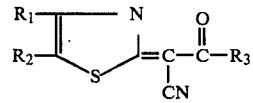

in which $R_1$, $R_2$ and $R_3$ have the meaning defined in the specification. The compounds are valuable as insecticides of a superior activity against specific groups of insects.

21 Claims, No Drawings

THIAZOLYLIDENE-OXO-PROPIONITRILES, INSECTICIDAL COMPOSITION CONTAINING THESE COMPOUNDS

BACKGROUND OF THE INVENTION

The invention relates to thiazolylidene-oxo-propionitriles, insecticidal compositions containing these compounds and process for making same.

Thiazolyl cinnamic acid nitriles with insecticidal activity have been disclosed in German published application No. 2,703,542. The action of these compounds, however, is not always adequate.

Likewise, compositions of a different chemical structure, but having similar activity are, for instance, phosphoric acid esters (West German Patent No. 814,152), chlorinated hydrocarbons (West German Patent No. 1,015,797), carbamates (U.S. Pat. No. 2,903,478) and pyrethroids (Belgian Patent No. 857,859). These agents have usually a broad range of activity.

The object of the present invention is rather the development of an insecticide which has a narrow spectrum of activity and can be used successfully for controlling specific insects.

ESSENCE OF THE INVENTION

This object is met by an insecticidal agent which contains one or more compounds of the formula

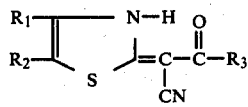

In this formula $R_1$ is hydrogen, halogen, $C_1$–$C_6$-alkyl, $C_3$–$C_6$-cycloalkyl, thienyl, pyridyl or an aromatic hydrocarbon residue substituted in one or several positions by the same or different radicals from the group constituted by $C_1$–$C_4$-alkyl, $C_1$–$C_4$-alkoxy, $C_1$–$C_4$-alkylthio, halogeno, trifluoromethyl, nitro and cyano.

$R_2$ is hydrogen, halogen, $C_1$–$C_6$-alkyl, $C_3$–$C_6$-cycloalkyl, thienyl, pyridyl, phenyl, or an aromatic hydrocarbon residue which is substituted in one or several positions by the same or different radicals selected from the group consisting of $C_1$–$C_4$-alkyl, $C_1$–$C_4$-alkoxy, $C_1$–$C_4$-alkylthio, halogeno, trifluoromethyl, nitro and cyano.

$R_3$ is an aromatic hydrocarbon residue which may also be substituted in one or several positions by the same or different radicals from the group consisting of $C_1$–$C_4$-alkyl, halogeno-$C_1$–$C_4$-alkyl, $C_1$–$C_4$-alkoxy, halogen, trifluoromethyl, nitro and cyano.

The compounds of the invention have a surprising insecticidal activity which partly is superior to the agents of analogous chemical constitution and they are highly effective against very specific insects.

A superior activity is found in the compounds of the invention, particularly against pests of the genera Coleopterans, Lepidopterans, Dipterans and Rhynchotens which are economically of great significance.

The compounds of the invention display their superior activity at concentrations of about 0.005 to 5.0%, preferably between 0.01 and 0.5%.

The compounds of the invention can either be used by themselves or intermixed with each other or with other insecticidal agents. If desired, other plant protection agents or pesticides such as acaricides or fungicides may be added depending on the specific objective.

An increase of the intensity of activity and speed of activity can, for instance, be accomplished by additives such as organic solvents, wetting agents, and oils. Such additives therefore may permit a lowering of the dosage of the primary effective agent.

The compounds or their mixtures are preferably used in the form of compositions such as powders, spraying agents, granulates, solutions, emulsions or suspensions. Liquid and/or solid carrier materials or diluents may be added and, if desired, wetting agents, adhesion promoting agents, emulsifier and/or dispersants, may also be added.

Suitable liquid carriers are, for instance, water, aliphatic and aromatic hydrocarbons and furthermore cyclohexanone, isophorone, dimethylsulfoxide, dimethylformamide, and mineral oil fractions.

As solid carrier materials there may be used mineral earths, for instance tonsil, silicagel, talc, kaolin, attaclay, limestone, silicic acid and plant products such as flours.

There may also be added surface active agents such as calciumlignosulfonate, polyoxyethylene-alkylphenylether, naphthalene sulfonic acids and their salts, phenolsulfonic acids and their salts, formaldehyde condensation products, fettyl alcoholsulfates, as well as substituted benzosulfonic acids and their salts.

The proportion of the active agent or agents in the different compositions can be varied within a broad range. The compositions may for instance contain about 5 to 95% by weight of active agent, about 95 to 5% by weight of liquid or carrier materials and, if desired, up to 20% by weight of surface active agents may be added upon a corresponding reduction of the carrier materials.

The application of the agents can be effected in conventional form, for instance with water as the carrier material in spray amounts of between 100 to 3000 l/ha (hectare=about 2.54 acres).

The application can be effected in the so-called low volume and ultra low volume procedure and also in the form of so-called microgranulates.

The making of these compositions can be effected in conventional form, for instance, by mixing or grinding processes. If desired, individual components can also be mixed only shortly prior to their use as this is for instance done in actual practice in the so-called tank mixing procedure.

Among the compounds of the invention, those are particularly outstanding with regard to their insecticidal action in which in the above equation $R_1$ is methylphenyl, halogenophenyl, tert.-butyl or thienyl, $R_2$ is hydrogen, and $R_3$ is phenyl substituted in one or two positions by the same or different radicals from the group consisting of methyl, fluoro, chloro, bromo, iodo, trifluoromethyl, nitro or methoxy.

The compounds of the invention can be made, for instance, by a process in which thiazolyl acetonitriles of the formula

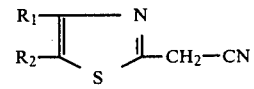

or their alkali salts are reacted with acid halides of the formula $R_3$—CO—X in which case the reaction may take place in an inert solvent upon addition of an organic base. $R_1$, $R_2$ and $R_3$ in these equations have the same significance as in the above broad formula of the final compounds. X is halogen and preferably chlorine.

The reaction preferably is carried out by heating a mixture of the reaction components to between 120° and 160° C. or a solution thereof in an inert solvent such as xylene to about 140° C. upon addition of catalytic amounts of an organic base, for instance, pyridine or 4-dimethylaminopyridine. If the alkali salts of the thiazolyl acetonitriles are used, the reaction preferably is carried out at a temperature of −10° C. to +40° C. in dimethylformamide, tetrahydrofuran or ether.

The following examples will further illustrate the making of the compounds:

EXAMPLE 1

3-(2-chloro-6-fluorophenyl)-2-(4-tert.-butyl-2,3-dihydrothiazol-2-ylidene)-3-oxopropionitrile 155 g (1.55 mol) of cyanothioacetamide dissolved in 17.1 of ethanol and 40° C. were reacted in a rapid operation with 280 g (1.55 mol) bromopinacoline and are subjected to boiling under reflux for 1 hour. After concentration in a vacuum the residue was treated with an aqueous sodium carbonate solution and extracted with methylene chloride. The organic phase was dried on magnesium sulfate, concentrated and distilled in a high vacuum.

The yield was 178 g=63% of the theoretical value of 4-tert.-butyl-2-cyanomethylthiazole.

bp$_2$: 101°–118° C.

9.0 g (0.05 mol) of the just obtained thiazol and 0.5 g of 4-dimethylaminopyridine were suspended in 20 ml xylene. After adding 9.7 g (0.05 mol) of 2-chloro-6-fluorobenzoylchloride the mass was subjected to boiling under reflux for 20 minutes. The solvent was distilled off in a vacuum and the residue was heated with 20 ml ethanol for 5 minutes. After further concentration in a vacuum recrystallization was effected from ethanol.

The yield was 5.1 g=30% of the theoretical value of 3-(2-chloro-6-fluorophenyl)-2-(4-tert.-butyl-2,3-dihydrothiazole-2-ylidene)-3-oxopropionitrile.

mp: 198°–199° C.

EXAMPLE 2

3-(2-chlorophenyl)-2-[4-(2-methylphenyl)-2,3-dihydrothiazole-2-ylidene]-3-oxopropionitrile A solution of 94 g (0.94 mol) of cyanothioacetamide in 1 l ethanol was slowly reacted at 40° C. upon stirring with 50.6 g (0.94 mol) of sodium ethylate. After 10 minutes 200 g (0.94 mol) of 2-methyl-ω-bromoacetophenone were added dropwise and the mass was then subjected to boiling upon reflux for 20 minutes.

The solution was concentrated in a vacuum and stirred into 4 l of water. The aqueous phase was extracted several times with ethylene chloride. The combined organic phases were dried on magnesium sulfate and concentrated in a vacuum. The oily residue was distilled in a high vacuum.

The yield was 76 g=38% of the theoretical value of 2-cyanomethyl-4-(2-methylphenyl)-thiazole.

bp$_{0.1}$: 159°–162° C.

10.7 g (0.05 mol) of the just obtained thiazole were suspended in 20 ml xylene and reacted with 0.5 g of 4-dimethyl-aminopyridine. After adding 8.8 g (0.05 mol) of 2-chlorobenzoyl chloride, the mass was boiled for 20 minutes upon reflux. The solvent was then removed in a vacuum and the mass was boiled with 20 ml methanol and again concentrated. The residue was recrystallized from acetonitrile.

The yield was 9.5 g=54% of the theoretical value of 3-(2-chlorophenyl)-2-(4-(2-methylphenyl)-2,3-dihydrothiazole-2-ylidene)-3-oxopropionitrile.

mp.: 168° C.

In an analogous manner the following compounds were made:

| Compound | Physical constants |
| --- | --- |
| 3-(2-methylphenyl)-2-(5-methyl-4-phenyl-2,3-dihydrothiazole-2-ylidene)-3-oxopropionitril | m.p.: 108–100° C. |
| 3-(2-fluorophenyl)-3-oxo-2-(4-tert.-butyl-2,3-dihydrothiazole-2-ylidene)-propionitrile | m.p.: 176–177° C. |
| 3-(2-chlorophenyl)-3-oxo-2-(4-tert.-butyl-2,3-dihydrothiazole-2-ylidene)-propionitrile | m.p.: 217–219° C. |
| 2-(4-tert.-butyl-2,3-dihydrothiazole-2-ylidene)-3-(2-trifluoromethylphenyl)-3-oxopropionitrile | m.p.: 195–196° C. |
| 3-(2-chlorophenyl)-3-oxo-2-[4-(2-thienyl)-2,3-dihydrothiazole-2-ylidene]-propionitrile | m.p.: 162–163° C. |
| 3-(2-bromophenyl)-3-oxo-2-[4-(2-thienyl)-2,3-dihydrothiazole-2-ylidene]-propionitrile | m.p.: 147–148° C. |
| 3-(2-fluorophenyl)-2-[4-(2-methylphenyl)-2,3-dihydrothiazole-2-ylidene]-3-oxopropionitrile | m.p.: 163–164° C. |
| 3-(2-chloro-6-fluorophenyl)-2-[4-(2-methylphenyl)-2,3-dihydrothiazole-2-ylidene]-3-oxopropionitrile | m.p.: 191–192° C. |
| 3-(2-bromophenyl)-2-[4-(2-methylphenyl)-2,3-dihydrothiazole-2-ylidene]-3-oxopropionitrile | m.p.: 167–168° C. |
| 3-(2-methoxyphenyl)-2-[4-(2-methylphenyl)-2,2-dihydrothiazole-2-ylidene]-3-oxopropionitrile | m.p.: 149–151° C. |
| 3-(2-iodophenyl)-2-[4-(2-methylphenyl)-2,3-dihydrothiazole-2-ylidene]-3-oxopropionitrile | m.p.: 165–166° C. |
| 3-(2-chlorophenyl)-2-[4-(3-methylphenyl)-2,3-dihydrothiazole-2-ylidene]-3-oxopropionitrile | m.p.: 157–158° C. |
| 2-[4-(2-chlorophenyl)-2,3-dihydrothiazole-2-ylidene]-3-oxo-3-phenylpropionitrile | m.p.: 170–170.5° C. |
| 3-(2-chlorophenyl)-2-[4-(2-chlorophenyl)-2,3-dihydrothiazole-2-ylidene]-3-oxopropionitrile | m.p.: 170–171° C. |
| 3-(2-chlorophenyl)-2-[4-(2-fluorophenyl)-2,3-dihydrothiazole-2-ylidene]-3-xoxpropionitrile | m.p.: 164–170° C. |
| 2-(5-bromo-4-phenyl-2,3-dihydrothiazole-2-ylidene)-3-(2-chlorophenyl)-3-oxopropionitrile | m.p.: 143° C. (decomposition) |
| 3-(2-chlorophenyl)-3-oxo-2-[4-(2-pyridyl)-2,3-dihydrothiazole-2-ylidene]-propionitrile | m.p.: 200–201° C. |

The compounds of the invention are usually practically insoluble in water and gasoline. They are moderately soluble in methanol, acetone and acetic acid ester and have a good solubility in dimethylformamide. They are crystalline bodies.

The following examples will further illustrate the application and activity of the compounds of the invention:

USE AND ACTIVITIES

EXAMPLE 3

The compounds of the inventions were used in this Example as aqueous suspensions in the concentration indicated in the Table below.

These active agents in the form of 4 mg of a spray/cm$^2$ were sprayed on cauliflower leaves disposed in polystyrene Petri dishes. After drying of the deposits 10 juvenile caterpillars of the cabbage moth (*Plutella maculipennis*), were placed into each Petri dish, and the Petri dishes were closed for 2 days to leave the caterpillars with the feed indicated.

In the Table below the criteria for the activity was the mortality of the caterpillars stated in percentage after 2 days.

| Compound | Concentration of active agents in % | Mortality in % |
|---|---|---|
| 3-(2-methylphenyl)-2-(5-methyl-4-phenyl-2,3-dihydrothiazole-2-ylidene)-3-oxopropionitrile | 0.1 | 100 |
| 3-(2-fluorophenyl)-3-oxo-2-(4-tert.-butyl-2,3-dihydrothiazole-2-ylidene)-propionitrile | 0.1 | 100 |
| 3-(2-chlorophenyl)-3-oxo-2-(4-tert.-butyl-2,3-dihydrothiazole-2-ylidene)-propionitrile | 0.1 | 100 |
| 3-(2-chloro-6-fluorophenyl)-2-(4-tert.-butyl-2,3-dihydrotiazole-2-ylidene)-3-oxopropionitrile | 0.1 | 100 |
| 2-(4-tert.-butyl-2,3-dihydrothiazole-2-ylidene)-3-(2-trifluoromethylphenyl)-3-oxopropionitrile | 0.1 | 100 |
| 3-(2-chlorophenyl)-3-oxo-2-[4-(2-thienyl)-2,3-dihydrothiazole-2-ylidene]-propionitrile | 0.1 | 100 |
| 3-(2-bromophenyl)-3-oxo-2-[4-(2-thienyl)-2,3-dihydrothiazole-2-ylidene]-propionitrile | 0.1 | 100 |
| 3-(2-chlorophenyl)-2-[4-(2-methylphenyl)-2,3-dihydrothiazole-2-ylidene]-3-oxopropionitrile | 0.1 | 100 |
| 3-(2-fluorophenyl)-2-[4-(2-methylphenyl)-2,3-dihydrothiazole-2-ylidene]-3-oxopropionitrile | 0.1 | 100 |
| 3-(2-chloro-6-fluorophenyl)-2-[4-(2-methylphenyl)-2,3-dihydrothiazole-2-ylidene]-3-oxopropionitrile | 0.1 | 100 |
| 3-(2-bromophenyl)-2-[4-(2-methylphenyl)-2,3-dihydrothiazole-2-ylidene]-3-oxopropionitrile | 0.1 | 100 |
| 3-(2-methoxyphenyl)-2-[4-(2-methylphenyl)-2,3-dihydrothiazole-2-ylidene]-3-oxopropionitrile | 0.1 | 100 |
| 3-(2-iodophenyl)-2-[4-(2-methylphenyl)-2,3-dihydrothiazole-2-ylidene]-3-oxopropionitrile | 0.1 | 100 |
| 3-(2-chlorophenyl)-2-[4-(3-methylphenyl)-2,3-dihydrothiazole-2-ylidene]-3-oxopropionitrile | 0.1 | 100 |
| 2-[4-(2-chlorophenyl)-2,3-dihydrothiazole-2-ylidene]-3-oxo-3-phenylpropionitrile | 0.1 | 100 |
| 3-(2-chlorophenyl)-2-[4-(2-chlorophenyl)-2,3-dihydrothiazole-2-ylidene]-3-oxopropionitrile | 0.1 | 100 |
| 3-(2-chlorophenyl)-2-[4-(2-fluorophenyl)-2,3-dihydrothiazole-2-ylidene]-3-oxopropionitrile | 0.1 | 100 |
| 2-(5-bromo-4-phenyl-2,3-dihydrothiazole-2-ylidene)-3-(2-chlorophenyl)-3-oxopropionitrile | 0.1 | 100 |
| 3-(2-chlorophenyl)-3-oxo-2-[4-(2-pyridyl)-2,3-dihydrothiazole-2-ylidene]-propionitrile | 0.1 | 100 |

EXAMPLE 4

The compounds of the invention were used in this example as aqueous suspensions in the concentration indicated in the Table below. The comparison compounds were likewise diluted with water so as to form suspensions or emulsions in the concentrations indicated.

These active agents were then sprayed in dosages of 4 mg spray amounts cm$^2$ into the lids and bottoms of polystyrene Petri dishes. To these spray deposits there were then exposed 25 adult Mediterranean fruit flies (*Ceratitis capitata*) per dish for 48 hours. The test was carried out in the laboratory with the Petri dishes closed and under conditions of a long-day illumination.

The criterium for the activity was the mortality of the flies expressed in percentages after 48 hours. The data appear from the following Table.

| Compound | Concentration of active agent in % | Mortality in % after 48 h |
|---|---|---|
| 2-(4-tert.-butyl-2,3-dihydrothiazole-2-ylidene)-3-(2-trifluoromethylphenyl)-3-oxopropionitrile | 0.0025 | 90 |
| 3-(2-chloro-6-fluorophenyl)-2-[4-(2-methylphenyl)-2,3-dihydrothiazole-2-ylidene]-3-oxopropionitrile | 0.0025 | 98 |
| 3-(2-iodophenyl)-2-[4-(2-methyl henyl)-2,3-dihydrothiazole-2-ylidene]-3-oxopropionitrile | 0.0025 | 95 |
| 3-(2-chlorophenyl)-2-[4-(2-chlorophenyl)-2,3-dihydrothiazole-2-ylidene]-3-oxopropionitrile | 0.0025 | 93 |
| COMPARISON COMPOUNDS | | |
| 2'-chloro-3-hydroxy-2-(4-phenyl-2-thiazolyl)-cinnamic acid nitrile (West German Patent OS 27 03 542) | 0.0025 | 73 |
| 2-(4-chlorophenyl)-isovaleric acid (α-cyano-3-phenoxybenzyl)-ester (Belgian Patent PS 857-859) | 0.0025 | 65 |
| 6,7,8,9,10,10-hexachloro-1,5,5a,6,9,9a-hexahydro-6,9-methano-2,4,3-benzodioxathiepine-3-oxyd (West German Patent 1,015,797) | 0.0025 | 68 |

EXAMPLE 5

The compounds of the invention were used as aqueous suspensions in the concentrations indicated below. The comparison compounds were likewise diluted with water and used as suspensions or emulsions in the indicated concentrations.

These active agents were then sprayed in amounts of 4 mg of spray amounts/cm² on cauliflower leaves disposed in polystyrene Petri dishes. After drying of the spray deposits there were placed ten juvenile caterpillars of the cabbage moth (*Plutella maculipennis*) into each dish and the caterpillars were then left for 2 days in the closed Petri dishes with the indicated feed.

The criterium for the activity was the mortality of the caterpillar expressed in percentages after 2 days. The data are compiled in the following Table.

| Compound | Concentration of active agent in % | Mortality in % |
|---|---|---|
| 3-(2-chloro-6-fluorophenyl)-2-(4-tert.-butyl-2,3-dihydrothiazole-2-ylidene)-3-oxopropionitrile | 0.01 | 100 |
|  | 0.005 | 65 |
| 3-(2-chloro-6-fluorophenyl)-2-4-(2-methylphenyl)-2,3-dihydrothiazole-2-ylidene- | 0.01 | 90 |
|  | 0.005 | 90 |
| COMPARISON COMPOUNDS | | |
| 2'-bromo-3-hydroxy-2-(4-phenyl-2-thiazolyl)-cinnamic acid nitrile (German published application 27 03 542) | 0.01 | 90 |
|  | 0.005 | 50 |
| 1-naphthyl-methylcarbamate (U.S. Pat. 2,903,478) | 0.01 | 50 |
|  | 0.005 | 10 |
| O,O-dimethyl-O-(p-nitrophenyl)-thiono-phosphoric acid ester (German Patent 814,152) | 0.01 | 70 |
|  | 0.005 | 50 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Thiazolylidene-oxo-propionitriles of the formula $$\begin{array}{c} R_1 \\ R_2 \end{array} \underset{S}{\underset{\|}{\diagdown}} {=} C {-} \underset{CN}{\overset{N-H}{\underset{|}{C}}} {-} \overset{O}{\underset{\|}{C}} {-} R_3$$

wherein
   $R_1$ is phenyl, methylphenyl, halogenophenyl, tert.-butyl, pyridyl or thienyl,
   $R_2$ is hydrogen, bromine or methyl, and
   $R_3$ is phenyl substituted in one or two positions by the same or different radicals selected from the group consisting of methyl, fluoro, chloro, bromo, iodo, trifluoromethyl, nitro or methoxy.

2. The compound of claim 1 which is 3-(2-chloro-6-fluorophenyl)-2-(4-tert.-butyl-2,3-dihydrothiazole-2-ylidene)-3-oxopropionitrile.

3. The compound of claim 1 which is 3-(2-chlorophenyl)-2-[4-(2-methylphenyl)-2,3-dihydrothiazole-2-ylidene]-3-oxopropionitrile.

4. The compound of claim 1 which is 3-(2-methylphenyl)-2-(5-methyl-4-phenyl-2,3-dihydrothiazole-2-ylidene)-3-oxopropionitrile.

5. The compound of claim 1 which is 3-(2-fluorophenyl)-3-oxo-2-(4-tert.-butyl-2,3-dihydrothiazole-2-ylidene)-propionitrile.

6. The compound of claim 1 which is 3-(2-chlorophenyl)-3-oxo-2-(4-tert.-butyl-2,3-dihydrothiazole-2-ylidene)-propionitrile.

7. The compound of claim 1 which is 2-(4-tert.-butyl-2,3-dihydrothiazole-2-ylidene)-3-(2-trifluoromethylphenyl)-3-oxopropionitrile.

8. The compound of claim 1 which is 3-(2-chlorophenyl)-3-oxo-2-[2-thienyl-2,3-dihydrothiazole-2-ylidene]-propionitrile.

9. The compound of claim 1 which is 3-(2-bromophenyl)-3-oxo-2-[4-(2-thienyl)-2,3-dihydrothiazole-2-ylidene]-propionitrile.

10. The compound of claim 1 which is 3-(2-fluorophenyl)-2-[4-(2-methylphenyl)-2,3-dihydrothiazole-2-ylidene]-3-oxopropionitrile.

11. The compound of claim 1 which is 3-(2-chloro-6-fluorophenyl)-2-[4-(2-methylphenyl)-2,3-dihydrothiazole-2-ylidene]-3-oxopropionitrile.

12. The compound of claim 1 which is 3-(2-bromophenyl)-2-[4-(2-methylphenyl)-2,3-dihydrothiazole-2-ylidene]-3-oxopropionitrile.

13. The compound of claim 1 which is 3-(2-methoxyphenyl)-2-[4-(2-methylphenyl)-2,3-dihydrothiazole-2-ylidene]-3-oxopropionitrile.

14. The compound of claim 1 which is 3-(2-iodophenyl)-2-[4-(2-methylphenyl)-2,3-dihydrothiazole-2-ylidene]-3-oxopropionitrile.

15. The compound of claim 1 which is 3-(2-chlorophenyl)-2-[4-(3-methylphenyl)-2,3-dihydrothiazole-2-ylidene]-3-oxopropionitrile.

16. The compound of claim 1 which is 2-[4-(2-chlorophenyl)-2,3-dihydrothiazole-2-ylidene]-3-oxo-3-phenyl-propionitrile.

17. The compound of claim 1 which is 3-(2-chlorophenyl)-2-[4-(2-chlorophenyl)-2,3-dihydrothiazole-2-ylidene]-3-oxopropionitrile.

18. The compound of claim 1 which is 3-(2-chlorophenyl)-2-[4-(2-fluorophenyl)-2,3-dihydrothiazole-2-ylidene]-3-oxopropionitrile.

19. The compound of claim 1 which is 2-(5-bromo-4-phenyl-2,3-dihydrothiazole-2-ylidene)-3-(2-chlorophenyl)-3-oxopropionitrile.

20. The compound of claim 1 which is 3-(2-chlorophenyl)-3-oxo-2-[4-(2-pyridyl)-2,3-dihydrothiazole-2-ylidene]-propionitrile.

21. An insecticidal composition comprising about 5 to 95% by weight of a compound as defined in claim 1 and about 95 to 5% by weight of liquid or solid carrier materials to which there may be added, upon corresponding reduction of the carrier materials, up to 20% by weight of surface active agents.

* * * * *